(12) United States Patent
Gupta et al.

(10) Patent No.: US 6,632,944 B2
(45) Date of Patent: Oct. 14, 2003

(54) PROCESS FOR ISOLATION OF MONOPHENOLIC-BISARYL TRIAZINES

(75) Inventors: Ram Baboo Gupta, Stamford, CT (US); Hargurpreet Singh, Ansonia, CT (US); Russell C. Cappadona, Norwalk, CT (US)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 09/887,128

(22) Filed: Jun. 22, 2001

(65) Prior Publication Data

US 2003/0013879 A1 Jan. 16, 2003

(51) Int. Cl.[7] .................... C07D 251/22; C07D 251/124
(52) U.S. Cl. ....................... 544/216; 544/219
(58) Field of Search ......................... 544/216

(56) References Cited

U.S. PATENT DOCUMENTS

| | | | |
|---|---|---|---|
| 3,242,175 A | 3/1966 | Duennenberger et al. | 260/248 |
| 3,244,708 A | 4/1966 | Duennenberger et al. | 260/248 |
| 3,268,474 A | 8/1966 | Hardy et al. | 260/45.8 |
| 3,394,134 A | 7/1968 | Duennenberger et al. | 260/248 |
| 4,092,466 A | 5/1978 | Fletcher et al. | 526/13 |
| 5,084,570 A | 1/1992 | Burdeska et al. | 544/216 |
| 5,106,972 A | 4/1992 | Burdeska et al. | 544/219 |
| 5,438,138 A | 8/1995 | Henneberger et al. | 544/217 |
| 5,726,310 A | 3/1998 | Orban et al. | 544/216 |
| 6,020,490 A | 2/2000 | Reinehr et al. | 544/216 |
| 6,225,468 B1 | 5/2001 | Gupta et al. | 544/216 |
| 6,239,275 B1 | 5/2001 | Gupta et al. | 544/213 |
| 6,239,276 B1 | 5/2001 | Gupta et al. | 544/213 |
| 6,242,597 B1 | 6/2001 | Gupta et al. | 544/216 |
| 6,242,598 B1 | 6/2001 | Stevenson et al. | 544/216 |

FOREIGN PATENT DOCUMENTS

| | | |
|---|---|---|
| EP | 0 941 989 A2 | 9/1999 |
| GB | 884802 | 12/1959 |
| JP | 97059263 | 3/1997 |
| WO | WO 00/29392 | 5/2000 |

OTHER PUBLICATIONS

H. Brunetti and C. E. Lüthi, "Die Synthese von asymmetrischsubstituierten o–Hydroxyphenyl–s–triazinen," Helvetica Chimica Acta—vol. 55, Fasc. 1 (1972) pp. 1566–1595.

Shigeo Tanimoto and Masato Yamagata, "Synthesis of Ultraviolet Absorber Having 2–(2–Hydroxyphenyl)–1,3, 5–Triazine Structure as a Funtional Moiety," Senyo to Yakahin, vol. 40(12), 1995, pp. 325–339.

R. Hirt, H. Nidecker and R. Berchtold, "Synthesen mit Cyanursäurechlorid," Helvitica Chimica Acta, vol. 33, (1950), pp. 1365–1369.

*Primary Examiner*—Mukund J. Shah
*Assistant Examiner*—Venkataraman Balasubramanian
(74) *Attorney, Agent, or Firm*—James A. Jubinsky; Claire M. Schultz; Valerie T. Didamo

(57) ABSTRACT

This invention relates to a novel, efficient, economic and general-purpose process for isolating monophenolic-bisaryl triazine compounds from polyphenolic-triazines compounds and other impurities. More specifically, this invention relates to a process for isolating the monophenolic-bisaryl triazine compounds by contacting it with a base, an alcohol or a hydrocarbon solvent.

37 Claims, No Drawings

PROCESS FOR ISOLATION OF MONOPHENOLIC-BISARYL TRIAZINES

FIELD OF THE INVENTION

This invention relates to a novel, efficient, economic and general-purpose process for isolating monophenolic-bisaryl triazine compounds from polyphenolic-triazines compounds and other impurities. More specifically, this invention relates to a process for isolating the monophenolic-bisaryl triazine compounds by contacting it with a base, an alcohol and/or a hydrocarbon solvent.

BACKGROUND OF THE INVENTION

Exposure to sunlight and other sources of ultraviolet (UV) radiation is known to cause degradation of a wide variety of materials, especially polymeric materials. For example, polymeric materials such as plastics often discolor and/or become brittle as a result of prolonged exposure to UV light. Accordingly, a large body of art has been developed directed towards materials such as UV light absorbers and stabilizers which are capable of inhibiting such degradation. Other areas of applications for the UV light absorbers include cosmetics (as sunscreen agents), fibers, spandex, inks, photographic materials, and dyes.

A class of materials known to be UV light absorbers are compounds which have aromatic substituents at the 2-, 4-, and 6-positions of the 1,3,5-triazine ring, and in which at least one of the aromatic rings has a hydroxyl substituent at the ortho position to the point of attachment to the triazine ring. In general, this class of compounds is well known in the art. Disclosures of a number of such triazine UV light absorbers (UVA's) as well as processes for preparing can be found in the following references and references cited therein, all of which are incorporated by reference as fully set forth herein: U.S. Pat. No. 6,239,275; U.S. Pat. No. 6,239,276; U.S. Pat. No. 6,242,597; U.S. Pat. No. 6,225,468 and WO 00/29392.

A preferred class of triazine UVA's are asymmetrical monophenolic-bisaryl triazines UVA's based on the 2-(2,4-dihydroxyaryl)-4,6-bisaryl-1,3,5-triazines, e.g., compounds where there are two non-phenolic aromatic groups, and one phenolic aromatic group that is derived from resorcinol, or substituted resorcinol. The 4-hydroxyl group of the parent compound, 2-(2,4-dihydroxyaryl)-4,6-bisaryl-1,3,5-triazine, is generally functionalized to make 2-(2-hydroxy-4-oxyaryl)-4,6-bisaryl-1,3,5-triazine derivatives for end use.

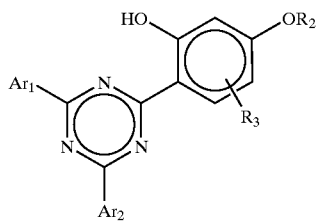

There are several approaches reported in the literature to make the preferred 2-(2,4-dihydroxyaryl)-4,6-bisaryl-1,3,5-triazine UVA's. (For a review of the previously known methods for making triazine UVA's, please see the following articles: 1. H. Brunetti and C. E. Luethi, *Helvetica Chimica Acta*, vol 55, 1972, pages 1566–1595; 2. S. Tanimoto and M. Yamagata, *Senryo to Yakahin*, vol. 40(12), 1995, pages 325–339.)

A majority of the approaches consists of three stages. The first stage, which can involve single or multi-steps from the commercial raw materials, deals with the preparation of the key intermediate, 2-chloro-4,6-bisaryl-1,3,5-triazine, which is subsequently arylated in the second stage with 1,3-dihydroxybenzene (resorcinol) or a substituted 1,3-dihydroxybenzene in the presence of Lewis acid to form the parent compound 2-(2,4-dihydroxyaryl)-4,6-bisaryl-1,3,5-triazine. The parent compound 2-(2,4-dihydroxyaryl)-4,6-bisaryl-1,3,5-triazine, as mentioned above, is generally functionalized further, e.g., alkylated, to make the final product 2-(2-hydroxy-4-oxyaryl)-4,6-bisaryl-1,3,5-triazine.

General Scheme for Making 2-(2-hydroxy-4-oxyaryl)-4,6-bisaryl-triazines

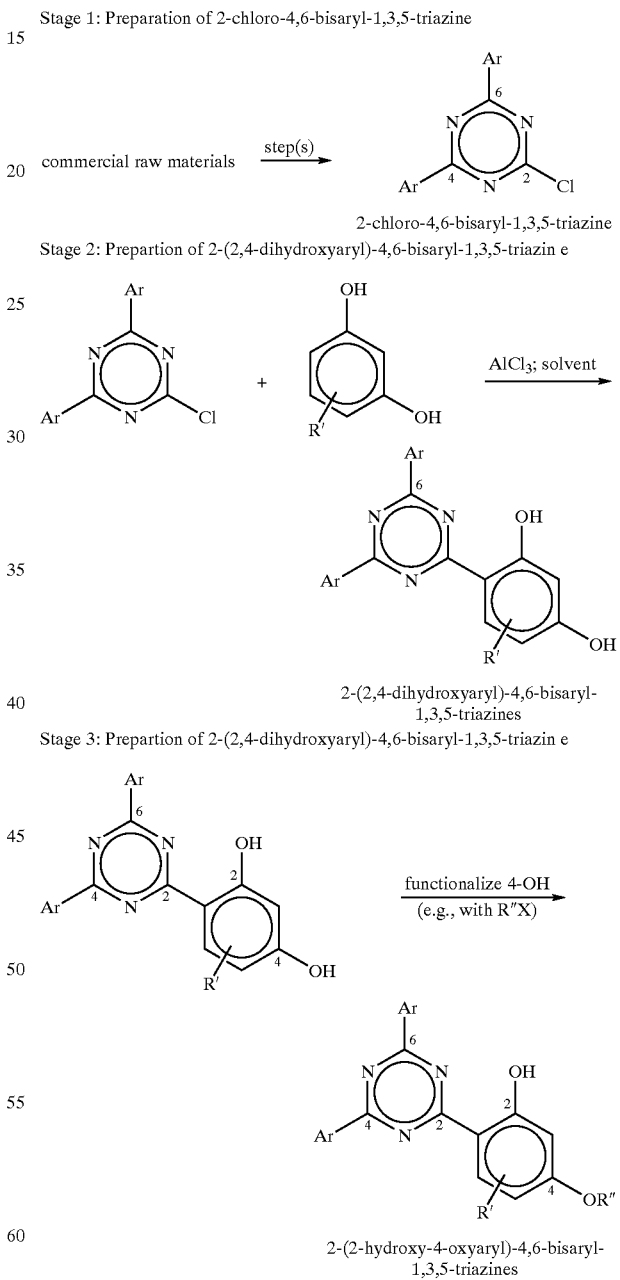

It has been recognized that the most versatile and economical method to prepare asymmetrical monophenolic-bisaryl triazine UVA's is to use a Friedel-Crafts reaction on cyanuric chloride with non-phenolic aromatics to first form 2-chloro-4,6-bisaryl-1,3,5-triazine, followed by another Friedel-Crafts reaction with the phenolic aromatic, in this case resorcinol, to make the desired monophenolic-bisaryl-triazine. However, it has been realized in the prior art (see, U.S. Pat. No. 3,394,134) that this known process as disclosed in U.S. Pat. No. 3,268,474 gives, only in exceptional cases, rise to the desired disubstituted derivatives of cyanuric chloride with some selectivity. Even when the aromatic compound and cyanuric chloride are reacted in molar proportions (1:1), the result is in general a mixture which contains mono-, di-, and tri-aryl substituted products, and, in addition, unreacted cyanuric chloride (U.S. Pat. No. 3,394,134) (Scheme 1).

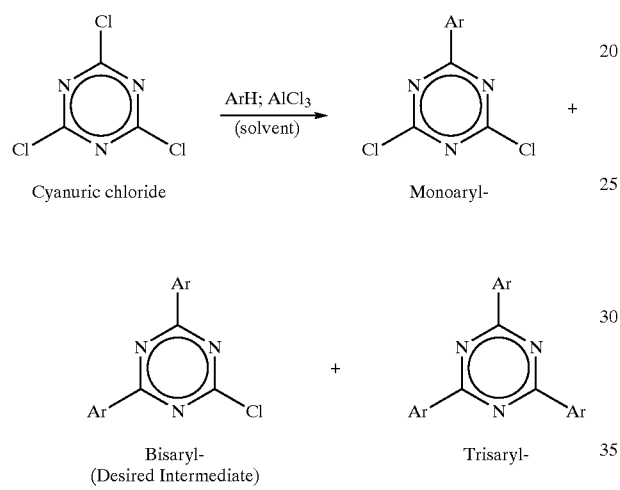

SCHEME 1
FIRST FRIEDEL-CRAFTS REACTION
WITH AROMATICS

Using the above mentioned process, a useful yield of the desired intermediate 2-chloro-4,6-bisaryl-1,3,5-triazine is obtained only with m-xylene as the aromatic reactant (GB 884802). 2-(2,4-dihydroxyphenyl)-4,6-bis(2,4-dimethylphenyl)-1,3,5-triazine, free of polyresorcinol-triazine impurities, was prepared from the isolated 2-chloro-4,6-bis(2,4-dimethylphenyl)-1,3,5-triazine that was purified by recrystallization, before reacting with resorcinol in a second step (see U.S. Pat. No. 3,244,708). The isolation and recrystallization of the 2-chloro-4,6-bis(2,4-dimethylphenyl)-1,3,5-triazine results in yield loss. With other aromatics, a difficult to separate mixture of all possible products are formed with no selectivity for the desired 2-chloro-4,6-bisaryl-1,3,5-triazine (For example, see H. Brunetti and C. E. Luethi, *Helvetica Chimica Acta,* vol 55, 1972, page 1575 and S. Tanimoto and M. Yamagata, *Senryo to Yakahin,* vol. 40(12),1995, pages 325–339).

When the reaction mixture from the first Friedel-Crafts reaction (Scheme 1) without any purification is treated in a subsequent Friedel-Crafts reaction with resorcinol, the bisaryl-derivative leads to the formation of desired monoresorcinol-bisaryl-triazine, and the monoaryl-substituted product leads to the formation of monoaryl-bisresorcinol derivative. Whereas, the unreacted cyanuric chloride leads to the formation of bis-and tris-resorcinol-triazine derivatives, i.e. polyresorcinol-triazines (see Scheme 2).

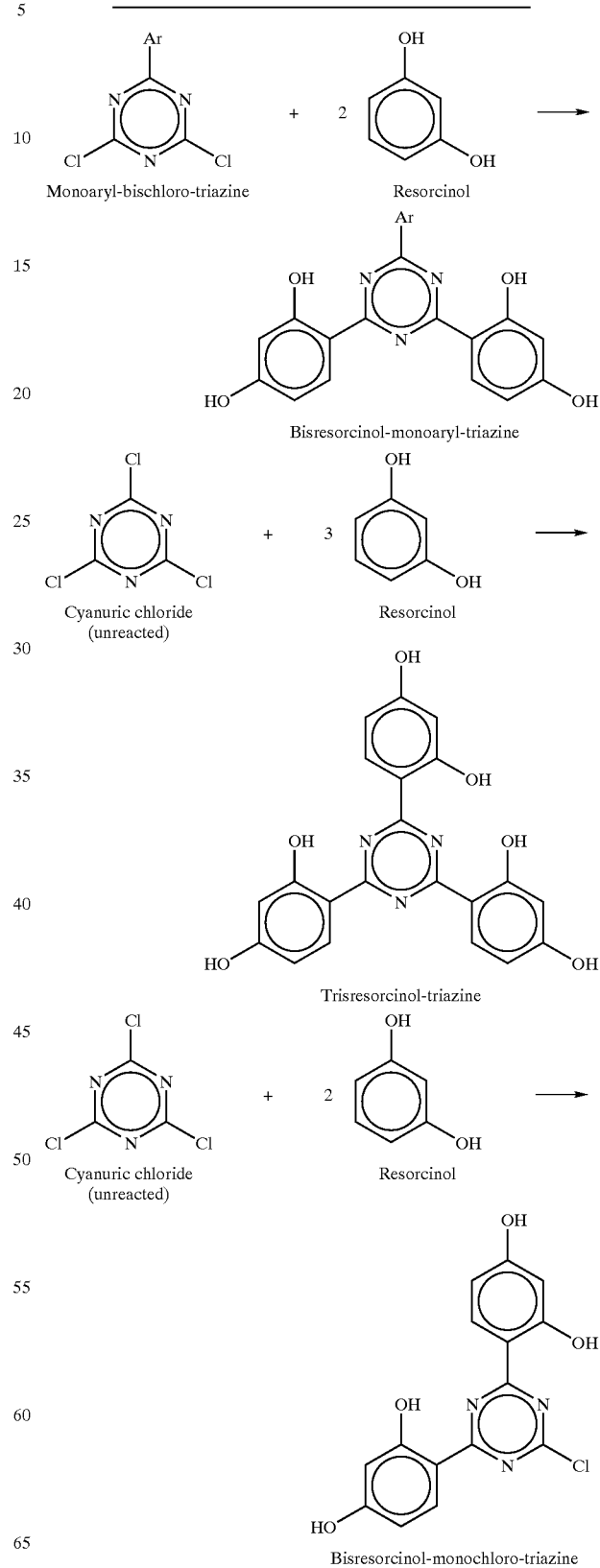

SCHEME 2
FORMATION OF POLYRESORCINOL TRIAZINE
IMPURITIES IN THE FRIEDEL-CRAFTS REACTION
WITH RESORCINOL

These polyresorcinol-triazine impurities (triazine ring with more than one resorcinol attached) lead to yellowing in the use of the UV absorbers prepared from the monoresorcinol-bisaryl-triazine in various polymer substrates, e.g., in polycarbonates, in lacquers, in automotive top-coatings, etc. Thus it is highly desirable for many such applications that the monoresorcinol-bisaryl-triazine derivative is free of these impurities. Unfortunately, there has been no process known in the literature to isolate monoresorcinol-bisaryl-triazine derivative from the mixture containing polyresorcinol impurities. The lack of selectivity for the bisaryl substitution in the Friedel-Crafts reaction of cyanuric chloride, coupled with the problems associated with the isolation of the bisaryl intermediate and the monoresorcinol-bisaryl-triazine derivative, had severely limited the usefulness of the most versatile and economic approach to the preferred class of triazine UVA's.

To overcome this obstacle, and to exclude the formation of polyresorcinol-triazines, other economically less attractive routes have been developed in which either cyanuric chloride was not used as starting material, and the triazine ring was synthesized by different methods, or the formation of polyresorcinol impurities was excluded by means of the circuitous routes (For example, see: A. Ostrogovich, Chemiker-Zeitung No. 78, page 738, 1912; von R. Hirt, H. Nidecker and R. Berchtold, Helvitica Chimica Acta, vol. 33, page 1365, 1950; H. Brunetti and C. E. Luethi, *Helvetica Chimica Acta*, vol 55, 1972, page 1575; U.S. Pat. No. 4,092,466; U.S. Pat. No. 5,084,570; U.S. Pat. No. 5,106,972; U.S. Pat. No. 5,438,138; U.S. Pat. No. 5,726,310; U.S. Pat. No. 6,020,490; EP 0941989 and Japanese Patent 09059263)

An alternate direct approach for the preparation of monoresorcinol-bisaryl-triazine as described in U.S. Pat. No. 6,225,468 B1 from cyanuric chloride also results in the formation of polyresorcinol products, and no method was disclosed to isolate the monoresorcinol-bisaryl-triazine product from the mixture.

More recently, a major breakthrough discovery in the field has led to the development of a process for making the desired bisaryl-monochloro-triazine with exceptionally high selectivity from the Friedel-Crafts reaction of cyanuric halide with aromatics in general (WO 00/29392). However, the selectivity is not 100%, and that still leads to the formation of small amounts of undesired polyresorcinol impurities, in the subsequent reaction with resorcinol in a one-pot process, and tris-aryl-triazine impurity.

As is apparent from the above discussion, it would be a very valuable and highly desirable addition in the field of triazine UV absorbers for a method to isolate monophenolic-bisaryl triazine that is free from the polyphenolic- or polyresorcinol-triazine impurities regardless of the synthesis process.

One of the advantages of the present invention is a highly efficient and very economical method of isolating monophenolic-bisaryl triazine that is substantially free from polyphenolic- or polyresorcinol-triazine impurities, irrespective of the process of its making, without the need for recrystallization. Thus the present invention also eliminates the need for purifying and isolating the intermediate 2-chloro-4,6-bisaryl-1,3,5-triazine from the first Friedel-Crafts reaction of aromatics with cyanuric chloride regardless of its selectivity, and allows to do the second Friedel-Crafts reaction with phenols, such as resorcinol, in a one-pot process to make monophenol-bisaryl-triazines.

Another advantage of the present invention is a method to isolate monophenolic-bisaryl triazine compounds from polyphenolic- or polyresorcinol-triazine, trisaryl-triazine, resorcinol (or substituted resorcinol), phenols, chlorobenzene or dichlorobenzene impurities.

SUMMARY OF THE INVENTION

The present invention relates to a process of isolating a compound of Formula 1

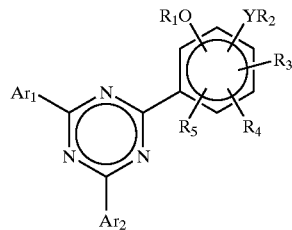

Formula 1 where $Ar_1$ and $Ar_2$ are the same or different and are radicals of the compound of Formula 2

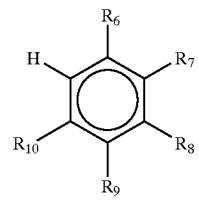

Formula 2 and where $R_1$ is hydrogen and $R_2$, $R_3$, $R_4$ and $R_5$, are the same or different and are hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, substituted or unsubstituted biphenylene, substituted or unsubstituted naphthalene, OR, NRR', CONRR', OCOR, CN, SR, $SO_2R$, and optionally with either of $R_3$ and $R_4$ or $R_4$ and $R_5$ taken together being a part of a saturated or unsaturated fused carbocyclic ring and where each R, R', $R_6$, $R_7$, $R_8$, $R_9$, and $R_{10}$ are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, substituted or unsubstituted biphenylene, substituted or unsubstituted naphthalene, and optionally with either of $R_6$ and $R_7$, $R_7$ and $R_8$, $R_8$ and $R_9$, or $R_9$ and $R_{10}$, taken together being a part of a saturated or unsaturated fused carbocyclic ring optionally containing O, N, or S atoms in the ring, and $R_6$, $R_7$, $R_8$, $R_9$, and $R_{10}$, may be an alkoxy of 1 to 24 carbons, and Y is a direct bond, O, NR", or SR" wherein R" is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms. The process involves the step of contacting a product mixture comprising the compound of Formula 1 with a base, an alcohol, a hydrocarbon solvent or mixtures thereof.

DETAILED DESCRIPTION OF THE INVENTION

The present involves a process for isolating a monophenolic-bisaryl triazine compound from polyphenolic- or polyresorcinol-triazine impurities. Typically, these impurities result from a synthesis reaction to make the monophenolic-bisaryl triazine compounds from a Friedel-Crafts based reaction as illustrated in General Scheme 1 and General Scheme 2 above. However, it should be noted that the present isolation process can be utilized to isolate monophenolic-bisaryl triazine compounds from polyphenolic- or polyresorcinol-triazine and other impurities in general and should not be limited to any particular synthesis route. In fact, the present process may be generally used to isolate monophenolic-bisaryl triazine compounds from polyphenolic- or polyresorcinol-triazine and other undesired compounds whether or not generated from a synthesis reaction.

The monophenolic-bisaryl triazine compound has the general Formula 1

Formula 1

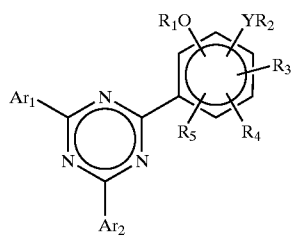

where $Ar_1$ and $Ar_2$ are the same or different and are radicals of the compound of Formula 2

Formula 2

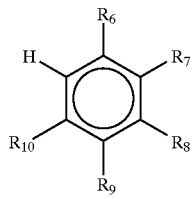

and where $R_1$ is hydrogen and $R_2$, $R_3$, $R_4$ and $R_5$, are the same or different and are hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, substituted or unsubstituted biphenylene, substituted or unsubstituted naphthalene, OR, NRR', CONRR', OCOR, CN, SR, $SO_2R$, and optionally with either of $R_3$ and $R_4$ or $R_4$ and $R_5$ taken together being a part of a saturated or unsaturated fused carbocyclic ring and where each R, R', $R_6$, $R_7$, $R_8$, $R_9$, and $R_{10}$ are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, substituted or unsubstituted biphenylene, substituted or unsubstituted naphthalene, and optionally with either of $R_6$ and $R_7$, $R_7$ and $R_8$, $R_8$ and $R_9$, or $R_9$ and $R_{10}$, taken together being a part of a saturated or unsaturated fused carbocyclic ring optionally containing O, N, or S atoms in the ring, and $R_6$, $R_7$, $R_8$, $R_9$, and $R_{10}$, may be an alkoxy of 1 to 24 carbons, and Y is a direct bond, O, NR", or SR", wherein R" is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms.

A preferred compound of Formula 1 is

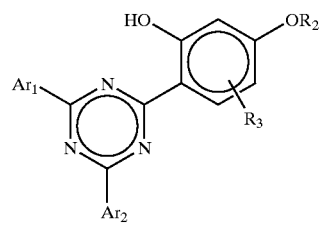

where $R_2$, $R_3$ is hydrogen, an alkyl of 1 to 24 carbon atoms or substituted alkyl of 1 to 24 carbon atoms.

A more preferred compound of Formula 1 is:

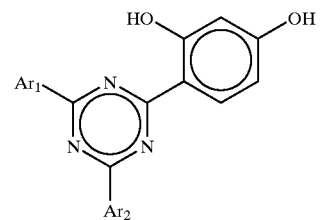

In one embodiment of the present invention, a "product mixture" which comprises the compound of Formula 1 as well as polyphenolic- or polyresorcinol-triazine and other impurities is contacted with a base. These impurities may result from a synthesis process where reactants, undesired by-products, entrained solvents, and the like, are agglomerated together with the desired compound of Formula 1. However, it should be noted that the product mixture does not have to result from a synthesis process and includes any mixture where the desired compound of Formula 1 is combined with undesired polyphenolic- or polyresorcinol-triazine compounds and other impurities.

The product mixture can be in solid or liquid form. For example, in the Friedel-Crafts reaction, the reaction is typically stopped by quenching with water to break the aluminum complex. The compound of Formula 1 and undesired impurities are precipitated out to form the product mixture in a solid form. This precipitated solid form may be directly added to the base, or dissolved with a solvent and added to the base. Any suitable solvent may be used to dissolve the product mixture. Examples of solvents that may be used to dissolve the product mixture include methylisobutylketone, methylethylketone, cyclohexanone, ethyl acetate, butyl acetate, methylene chloride, chloroform, carbon tetrachloride, 1,2-dichloroethane, chlorobenzene, dichlorobenzene, toluene, xylenes and mixtures thereof.

The bases that are suitable to be used in the present invention include inorganic bases, organic bases and mixtures thereof. Inorganic bases include LiOH, NaOH, KOH, $Mg(OH)_2$, $Ca(OH)_2$, $Zn(OH)_2$, $Al(OH)_3$, $NH_4OH$, $Li_2CO_3$, $Na_2CO_3$, $K_2CO_3$, $MgCO_3$, $CaCO_3$, $ZnCO_3$, $(NH_4)_2CO_3$, $BaCO_3$, $CaMg(CO_3)_2$, $NaHCO3$, $KHCO3$, (CaO), BaO, $LiNH_2$, $NaNH_2$, $KNH_2$, $Mg(NH_2)_2$, $Ca(NH_2)_2$, $Zn(NH_2)_2$, $Al(NH_2)_3$, NaH, CaH2, KH, LiH, and mixtures thereof.

Organic bases include hydrocarbon compounds with $C_1$–$C_9$ cyclic or non-cyclic that contain at least one alkoxide, amine, amide, carboxylate, or thiolate and which may be substituted in one or more positions with a halide, an hydroxyl, an ether, a polyether, a thiol, a thioether, an amine, such as —NHR, —NR'$_2$, —NRR', a carboxylic acid, an ester, or an amide. Preferably, the organic base is an amine that is primary, secondary, tertiary, aliphatic, cyclic, acyclic, aromatic, heteroaromatic, or heterocyclic; or salts of primary amine, secondary amine, alcohol, or acid. Organic bases include $CH_3O^-$, $CH_3CH_2O^-$, $CH_3CH_2CH_2O^-$, $(CH_3)_2CHO^-$, $((CH_3)_2CH)_2CHO^-$, $CH_3CH_2CH_2CH_2O^-$, $(CH_3)_3CO^-$, $CH_3NH^-$, $CH_3CH_2NH^-$, $CH_3CH_2CH_2NH^-$, $(CH_3)_2CHNH^-$, $((CH_3)_2CH)_2CHNH^-$, $CH_3CH_2CH_2CH_2NH^-$, $(CH_3)_3CNH^-$, $(CH_3)_2N^-$, $(CH_3CH_2)_2N^-$, $(CH_3CH_2CH_2)_2N^-$, $((CH_3)_2CH)_2N^-$, $(((CH_3)_2CH)_2CH)_2N^-$, $(CH_3CH_2CH_2CH_2)_2N^-$, $((CH_3)_3C)_2N^-$, formate, acetate, propylate, butanoate, benzoate; and $CH_3NH_2$, $CH_3CH_2NH_2$, $CH_3CH_2CH_2NH_2$, $(CH_3)_2CHNH_2$, $((CH_3)_2CH)_2CHNH_2$, $CH_3CH_2CH_2CH_2NH_2$, $(CH_3)_3CNH_2$, $(CH_3)_2NH$, $(CH_3CH_2)_2NH$, $(CH_3CH_2CH_2)_2NH$, $((CH_3)_2CH)_2NH$, $((CH_3)_2CH)_2EtN$, $(((CH_3)_2CH)_2CH)_2NH$, $(CH_3CH_2CH_2CH_2)_2NH$, $((CH_3)_3C)_2NH$, $(CH_3)_3N$, $(CH_3CH_2)_3N$, $(CH_3CH_2CH_2)_3N$, $((CH_3)_2CH)_3N$, $(((CH_3)_2CH)_2CH)_3N$, $(CH_3CH_2CH_2CH_2)_3N$, $((CH_3)_3C)_3N$, pyrrolidine, piperidine, N-alkylpiperidine, piperazine, N-alkylpiperazine, N,N-dialkylpiperazine, morpholine, N-alkylmorpholine, imidazole, pyrrole, pyridine, lutidine, 4-N,N-dimethylaminopyridine, aniline, N,N-dialkylaniline, tetramethylenediamine and mixtures thereof. Organic bases also includes salts of deprotonated carboxylic acids such as salts of formate, acetate, propylate, butanoate, benzoate, with Li, Na, K, Mg, Ca, Al, Zn, or any other suitable cation.

The suitable bases may be dissolved, if desired, in water, an organic solvent, or a mixture of solvents before or after contacting with the product mixture. Examples of suitable solvents include, but are not limited to water, alcohols, acetonitrile, tetrahydrofuran, toluene, heptane and mixtures thereof.

The amount of base to be added to the isolation blend should be enough to adjust the pH of the blend to between about 7.0 to about 14, preferably between about 9 to about 12.

The temperature of the base isolation step may be carried out at temperatures between about 10° C. and about the reflux temperature of the isolation blend. Preferably, the temperature is at about 40° C. to about the reflux temperature, or about 60° to about the reflux temperature.

Preferably, the isolation blend is mixed or stirred by any suitable method such as flow or line mixers, or in agitated vessels using mechanical or gas agitation.

The amount of time needed for the isolation step is between about 10 minutes and about 10 hours, more typically between about 1 to about 4 hours and about 1 to about 2 hours. If heat is used in the isolation step, the isolation blend may be allowed to cool.

If the product mixture is contacted with the base in solid form, the isolation blend after the isolation step is typically filtered to isolate the compound of Formula 1. Although not wishing to be bound by any theory, it is believed that the base solubilizes many of the polyphenolic- or polyresorcinol-triazine compounds and halogen-containing impurities used in the typical Friedel-Crafts reaction such that the solid mass after the isolation step contains mainly the compound of Formula 1 and trisaryl-triazines. The filtrate will be rich in the polyphenolic- or polyresorcinol-triazines and halogen-containing impurities. Impurities in the typically Friedel-Crafts reaction that is believed to be solubilized by the base include, but are not limited to compounds with the following formulas:

Impurities in General

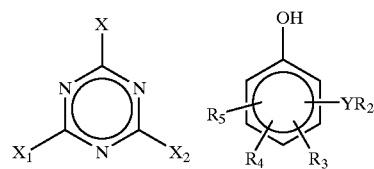

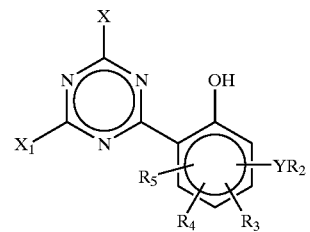

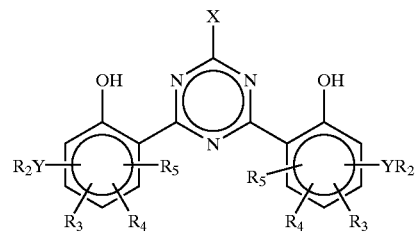

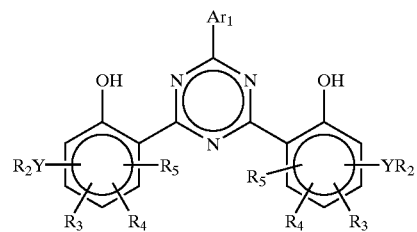

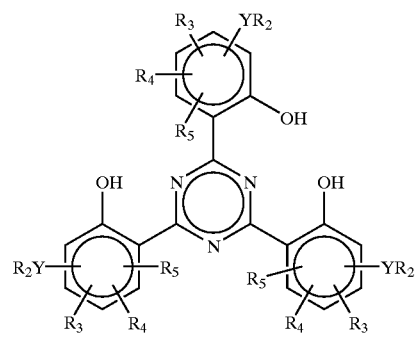

where X, $X_1$, $X_2$ is a halogen or hydroxy and the other substituents are defined above.

Preferred impurities which are solubilized by the base are:

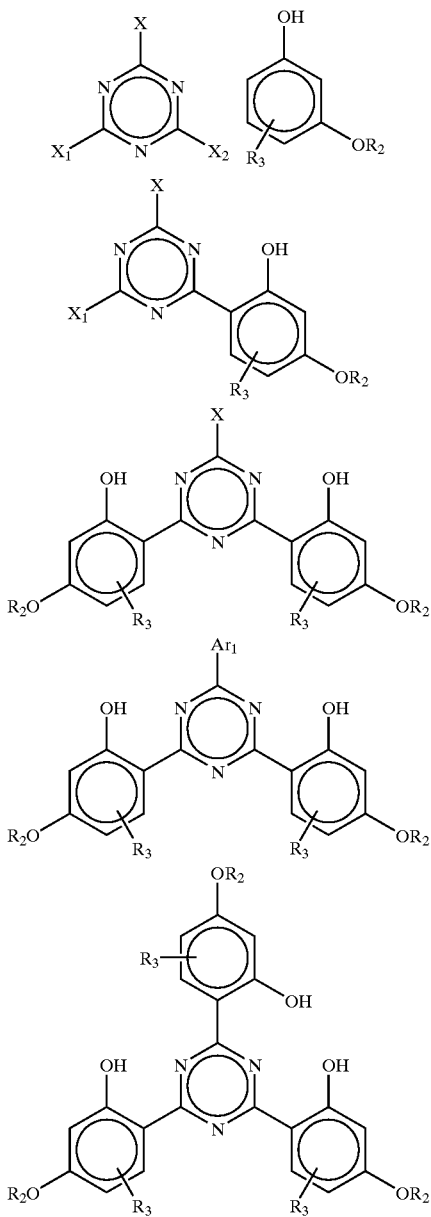

If a solvent is used to dissolve the product mixture, it is preferred that the solvent used to dissolve the base is substantially immiscible with the solvent used to dissolve the product mixture such that at least two distinct layers are formed. Preferably, the solvent used to dissolve the base is aqueous-based and the solvent used to dissolve the product mixture is organic-based. After the isolation step, it is believed that the aqueous-based layer will contain most of the halogen and polyresorcinol impurities, while the organic-based layer will contain mainly the compound of Formula 1 and trisaryl triazine compounds that are not soluble in the aqueous-based layer. The aqueous-based layer may be removed by any suitable process to leave the organic layer rich in the compound of Formula 1.

Typically, the base isolation step involves treating the reaction mixture such that is "substantially free" of polyphenolic- or polyresorcinol-triazines and halogen-containing impurities. "Substantially free" in the present application means that at least about 80% of the undesired impurities are removed from the reaction mixture during the isolation step. Preferably the amount of impurities removed are at least about 90%, more preferably at least about 95% and even more preferably at least about 98%.

It should be noted that the base isolation step of the present invention may also be used to isolate the polyphenolic- or polyresorcinol-triazine compounds. As mentioned above, the filtrate or the aqueous-based layer is rich in polyphenolic-triazine compounds. If an acid is added to the filtrate or aqueous-based layer, the polyphenolic-triazine compounds precipitate out to a solid form and may be filtered. Any suitable organic or inorganic acid may be used to precipitate the polyphenolic- or polyresorcinol-triazine compounds. Preferably, an inorganic acid is used. Examples of such inorganic acids include, but are not limited to: HCl, HBr, HI, $HNO_3$, $HNO_2$, $H_2S$, $H_2SO_4$, and $H_3PO_4$.

Alternatively, after the acidification of the filtrate, the polyphenolic- or polyresorcinol-triazine compounds may be isolated from the aqueous layer by solvent extraction. Any suitable solvent may be used for the solvent extraction. Examples of such suitable solvents include, but are not limited to: ethyl acetate, butyl acetate, dichloromethane and dichloroethane.

In another embodiment of the present invention, the product mixture containing the compound of Formula 1 in solid form is contacted with a hydrocarbon solvent to remove trisaryl-triazine impurities. Suitable hydrocarbon solvents include $C_1$–$C_{20}$ hydrocarbon compounds, saturated or unsaturated, cyclic or non-cyclic, and aromatic or non-aromatic. Examples of hydrocarbon solvent that may be used include, but are not limited to: benzene, toluene, ethylbenzene, diethylbenzene, xylene, mesitylene, tetralin, hexane, heptane, octane, cyclohexane, and mixtures thereof.

The amount of said hydrocarbon solvent present in the isolation step is about 1 to about 20 parts per part compound of Formula 1, preferably about 3 to about 10 parts hydrocarbon solvent per part compound of Formula 1.

The temperature of the hydrocarbon solvent isolation step is not critical and may be carried out at temperatures between about 10° C. to about the reflux temperature of the isolation blend. Preferably, the temperature is about 40° C. to about the reflux temperature, or about 60° C. to about the reflux temperature of the isolation blend.

The amount of time needed for the isolation step is typically between about 10 minutes to about 10 hours, more typically between about 1 to about 4 hours or about 1 to about 2 hours. If heat is used in the isolation step, the isolation blend is preferably allowed to cool.

Preferably, the isolation blend is mixed or stirred by any suitable method such as flow or line mixers, or in agitated vessels using mechanical or gas agitation.

After the isolation step, the isolation blend is typically filtered to isolate the compound of Formula 1.

Although not wishing to be bound by any theory, it is believed that the hydrocarbon solvent solubilizes the trisaryl triazine compounds from the solid form leaving it richer in the compound of Formula 1 after the isolation step. Typically, the hydrocarbon solvent isolation step involves treating the reaction mixture such that is substantially free of trisaryl-triazine impurities. The filtrate can be concentrated to isolate trisaryl-triazine.

Preferably, the base isolation step and the hydrocarbon isolation step are both used together either in a one-step or in a step-wise fashion, in any order, to isolate the compound of Formula 1. In the present application, the term "step-wise" means a series of isolations steps are conducted. The term "one-step" means when only one isolation step is conducted.

In another embodiment of the present invention, the product mixture containing the compound of Formula 1 is contacted with an alcohol. The product mixture preferably is in solid form. The isolation blend is heated to a temperature of about 40° C. to about 200° C., preferably about 60° C. to about 200° C., and more preferably to the reflux temperature of the blend. This isolation step is conducted for a period of about 10 minutes to 10 hours, preferably about 1 to about 4 hours or about 1 to about 2 hours. Preferably, the blend is allowed to cool to below about 40° C. If the product mixture is in solid form during this alcohol isolation step, the blend would be typically filtered to isolate the compound of Formula 1.

Any suitable alcohol may be used in this embodiment. Suitable alcohol compounds include carbon compounds of $C_1$–$C_{20}$, straight chain or branched, saturated or unsaturated, cyclic or non-cyclic, aromatic or non-aromatic, which has at least one hydroxyl group. Examples of suitable alcohol compounds include, but are not limited to: methanol, ethanol, propanol, isopropanol, butanol, isobutanol, t-butanol, 1,2-ethanediol, 3-chloro-1-propanol, 2-hydroxyl-acetic acid, 1-hydroxyl-3-pentanone, cyclohexanol, cyclohexenol, glycerol, benzyl alcohol and mixtures thereof.

The amount of alcohol added in the isolation step is about 1 to about 20 parts per part compound of Formula 1, preferably about 3 to about 10 parts alcohol to per part compound of Formula 1.

Preferably, the isolation blend is mixed or stirred by any suitable method such as flow or line mixers, or in agitated vessels using mechanical or gas agitation.

Although not wishing to be bound by any theory, it is believed that the alcohol solubilizes many of the polyresorcinol and halogen containing impurities used in the typical Friedel-Crafts reaction such that the solid mass after the isolation step contains mainly the compound of Formula 1 and reduced levels of trisaryl-triazines. Typically, the alcohol isolation step involves treating the reaction mixture such that it is substantially free of polyresorcinol and halogen-containing impurities. The alcohol soluble filtrate can be concentrated to recover polyresorcinol-triazines.

It should be noted that it is possible to dissolve the solid product mixture in an organic solvent in this alcohol isolation process. Preferably, the solvent used to dissolve the product mixture is immiscible with the alcohol such that at least two distinct layers are formed. It may be necessary to add some water to the alcohol to form the separate layers. It is believed that the alcohol-based layer will contain most of the halogen and polyresorcinol impurities, and the organic-based layer will contain mainly the compound of Formula 1 and trisaryl triazine compounds that are not soluble in the alcohol-based layer. The alcohol-based layer may be removed by any suitable process to leave the organic layer rich in the compound of Formula 1.

Preferably, the alcohol isolation step and the hydrocarbon isolation step are both used together either in a one-step or in a step-wise fashion, in any order, to isolate the compound of Formula 1.

In another embodiment of the present invention, the product mixture comprising the compound of formula 1 is contacted with at least two components selected from the group consisting of a base, an alcohol and a hydrocarbon solvent. The same processing conditions and amounts as described above may be used in this embodiment. The contacting may be performed in a step-wise or one-step fashion. Preferably, either the base and hydrocarbon solvent components, or the alcohol and hydrocarbon solvent components are processed together.

EXAMPLES

Certain embodiments and features of the invention are illustrated, and not limited, by the following working examples.

Example 1

Isolation of 2-(2,4-dihydroxyphenyl)-4,6-bis(2,4-dimethylphenyl)-1,3,5-triazine by Treating with 5% Aqueous Sodium Carbonate a. Preparation of 2-(2,4-dihydroxyphenyl)-4,6-bis(2,4-dimethylphenyl)-1,3,5-triazine (following a procedure in WO 00/29392)

To a reaction flask equipped with a reflux condenser, a nitrogen inlet, and a mechanical stirrer was added 50 g of cyanuric chloride, 191 mL of ortho-dichlorobenzene (ODCB), and 108.5 gm of aluminum chloride. The mixture was cooled in an ice-bath to 5° C. and 6.5 gm of concentrated HCl was added over a period of 20 minutes. The mixture was allowed to warm room to temperature, and stirred for 2 hours. It was cooled back to 5° C. and then 51.8 gm of m-xylene was slowly added over a period of 4 hours, while allowing the temperature to go up to 21° C. The mixture was stirred at room temperature for additional 16 hours. The reaction mixture was heated to about 69° C. and 32.8 gm of resorcinol was added over a period of 30 minutes. The mixture was held at about 65° C. for 4 hours. It was then added to 500 mL water and ODCB distilled off azeotropically. The precipitated solid was filtered off to give 120 gm of water wet 2-(2,4-dihydroxyphenyl)-4,6-bis(2,4-dimethylphenyl)-1,3,5-triazine. The HPLC analysis showed it to contain about 7% of polyresorcinols consisting mainly of trisresorcinol-triazine and bisresorcinol-monochloro-triazine.

b. Isolation of 2-(2,4-dihydroxyphenyl)-4,6-bis(2,4-dimethylphenyl)-1,3,5-triazine To a reaction flask equipped with a reflux condenser, a Dean-Stark apparatus, a nitrogen inlet, and a mechanical stirrer was added 225 mL water and 11.25 gm of sodium carbonate. To the resulting solution was then added 100 gm crude 2-(2,4-dihydroxyphenyl)-4,6-bis(2,4-dimethylphenyl)-1,3,5-triazine, (about 50% wet) bisaryl-monoresorcinol-triazine prepared by procedure of Example 1a containing polyresorcinol-triazines as impurities. The pH of the mixture was about 10. The resulting mixture was heated to reflux, and it was held at reflux for 2 hours while residual ODCB was collected as azeotropic mixture in the Dean-Stark apparatus. The heating was discontinued, and the mixture filtered around 50 to 60° C. The filter cake was twice washed with 112.5 mL of 5% aqueous sodium carbonate solution followed by 600 mL of 50° C. water, and filtered to give 97.5 gm of 2-(2,4-dihydroxyphenyl)-4,6-bis(2,4-dimethylphenyl)-1,3,5-triazine (about 50% wet). The HPLC analysis showed no detectable amounts of polyresorcinol-triazines remaining in 2-(2,4-dihydroxyphenyl)-4,6-bis(2,4-dimethylphenyl)-1,3,5-triazine. It was also free of ODCB.

The filtrate was analyzed by HPLC to contain no 2-(2,4-dihydroxyphenyl)-4,6-bis(2,4-dimethylphenyl)-1,3,5-triazine.

Example 2

Isolation of 2-(2,4-dihydroxyphenyl)-4,6-bis(2,4-dimethylphenyl)-1,3,5-triazine by Treating with 3% Aqueous Sodium Carbonate To a reaction flask equipped with a reflux condenser, a Dean-Stark apparatus, a nitrogen inlet, and a mechanical stirrer was added 112.5 mL of 3% aqueous sodium carbonate and 50 gm crude 2-(2,4-dihydroxyphenyl)-4,6-bis(2,4-dimethylphenyl)-1,3,5-triazine from Example 1a containing polyresorcinol-triazines as impurities. The resulting mixture was heated to reflux, and it was held at reflux for 2 hours while residual ODCB was collected as azeotropic mixture in the Dean-Stark apparatus. The heating was discontinued, and the mixture filtered around 80° C. The filter cake was washed with 112.5 mL of 3% aqueous sodium carbonate solution followed by 300 mL of 50° C. water. The 47 gm of residue thus obtained was analyzed by HPLC to be 2-(2,4-dihydroxyphenyl)-4,6-bis(2,4-dimethylphenyl)-1,3,5-triazine containing no polyresorcinol impurities.

a. Isolation of Polyresorcinol-triazine

The filtrate was acidified with aqueous HCl, and extracted with ethyl acetate. The organic layer was analyzed by HPLC which showed it to contain mainly polyresorcinol-triazines, with almost no 2-(2,4-dihydroxyphenyl)-4,6-bis(2,4-dimethylphenyl)-1,3,5-triazine.

Example 3

Isolation of 2-(2,4-dihydroxyphenyl)-4,6-bis(2,4-dimethylphenyl)-1,3,5-triazine by Treating with Aqueous Sodium Hydroxide To a reaction flask equipped with a reflux condenser, a Dean-Stark apparatus, a nitrogen inlet, and a mechanical stirrer was added 50 gm of crude 2-(2,4-dihydroxyphenyl)-4,6-bis(2,4-dimethylphenyl)-1,3,5-triazine prepared by procedure of Example 1a containing polyresorcinol-triazines as impurities, followed by 175 mL of 0.25% aqueous sodium hydroxide solution. The reaction mixture was heated to reflux while residual ODCB was collected as azeotropic mixture in the Dean-Stark apparatus. An additional 175 mL of 0.25% aqueous sodium hydroxide was added to maintain the pH at about 10, and the refluxing continued for another hour. The heating was discontinued. The mixture was filtered, the filter cake washed first with 300 mL of 0.25% aqueous sodium hydroxide solution, followed by 500 mL water. The HPLC analysis of the product (47 gm) thus obtained showed no detectable amounts of polyresorcinol-triazines remaining in 2-(2,4-dihydroxyphenyl)-4,6-bis(2,4-dimethylphenyl)-1,3,5-triazine.

Example 4

Removal of Resorcinol and Polyresorcinol Impurities from 2-(2,4-dihydroxyphenyl)-4,6-bis(2,4-dimethylphenyl)-1,3,5-triazine A mixture of 5 gm of 2-(2,4-dihydroxyphenyl)-4,6-bis(2,4-dimethylphenyl)-1,3,5-triazine, 250 mg of resorcinol and 200 mg of polyresorcinol-triazines (polyresorcinol-triazines were prepared by reacting cyanuric chloride with resorcinol using $AlCl_3$) was heated with 50 mL of 5% aqueous sodium carbonate solution. The mixture was heated to reflux for 3 hours. The heating was discontinued, and the mixture was filtered, the filter cake washed first with 5% aqueous sodium carbonate solution followed by with water. The 4.6 gm of the solid product thus obtained was analyzed by HPLC to be 2-(2,4-dihydroxyphenyl)-4,6-bis(2,4-dimethylphenyl)-1,3,5-triazine and contained no resorcinol or polyresorcinol-triazines.

Example 5

Removal of Cyanuric Chloride from 2-(2,4-dihydroxyphenyl)-4,6-bis(2,4-dimethylphenyl)-1,3,5-triazine Using 2% Aqueous Sodium Hydroxide To a mixture of 9 gm 2-(2,4-dihydroxyphenyl)-4,6-bis(2,4-dimethylphenyl)-1,3,5-triazine and 1 gm cyanuric chloride in a flask equipped with magnetic stirrer, a nitrogen inlet and a reflux condenser was added 60 mL of 5% aqueous sodium carbonate. The mixture was heated to reflux for 2 hours. The heating was discontinued, the mixture was filtered, and the filter cake was washed first with 5% aqueous sodium carbonate, then with water, and dried to give 8.8 gm of 2-(2,4-dihydroxyphenyl)-4,6-bis(2,4-dimethylphenyl)-1,3,5-triazine. The product was analyzed by HPLC to be free of cyanuric chloride.

Example 6

Removal of Resorcinol, Cyanuric Chloride and Polyresorcinol-triazine from 2-(2,4-dihydroxyphenyl)-4,6-bis(2,4-dimethylphenyl)-1,3,5-triazine Using 2% Aqueous Sodium Hydroxide To a mixture of 10 gm crude 2-(2,4-dihydroxyphenyl)-4,6-bis(2,4-dimethylphenyl)-1,3,5-triazine containing polyresorcinol-triazines, 1 gm resorcinol and 1 gm cyanuric chloride in a flask equipped with magnetic stirrer, a nitrogen inlet and a reflux condenser was added 75 mL of 2% aqueous sodium hydroxide. The mixture was heated to reflux for 1 hour. The pH of the mixture was about 11. The heating was discontinued, the mixture cooled to room temperature and filtered. The filter cake was washed first with 50 mL of 2% aqueous sodium hydroxide, then three times with 50 mL water, and then dried to give 9.4 gm of 2-(2,4-dihydroxyphenyl)-4,6-bis(2,4-dimethylphenyl)-1,3,5-triazine that was free of cyanuric chloride, resorcinol and polyresorcinol-triazine impurities by HPLC analysis.

Example 7

Isolation of 2-(2,4-dihydroxyphenyl)-4,6-bis(2,4-dimethylphenyl)-1,3,5-triazine and Polyresorcinol-triazines a. Preparation of 2-(2,4-dihydroxyphenyl)-4,6-bis(2,4-dimethylphenyl)-1,3,5triazine with High Levels of Polyresorcinol-triazines To a reaction flask equipped with a reflux condenser, a nitrogen inlet, and a magnetic stirrer was added 2 gm of cyanuric chloride, 25 mL chlorobenzene, 4.4 gm of aluminum chloride and 2.34 gm of m-xylene. The reaction mixture was stirred at room temperature for about 40 hours. To it was then added 3.6 gm of resorcinol and heated to 90° C. for 2 hours. The reaction mixture was quenched with water, and chlorobenzene removed azeotropically. The precipitated material was filtered, the filter cake washed with water and dried to give 4.5 gm of a crude product. The HPLC analysis showed that the product mixture contained a total of 62% of polyresorcinols (consisting of about 53% of trisresorcinol-triazine, 9% of bisresorcinol-monoxylyl-triazine), and only 34% of 2-(2,4-dihydroxyphenyl)-4,6-bis(2,4-dimethylphenyl)-1,3,5-triazine.

b. Isolation of 2-(2,4-dihydroxyphenyl)-4,6-bis(2,4-dimethylphenyl)-1,3,5-triazine To a reaction flask, 1 gm of the above mixture in Example 7a was heated with 30 mL of 5% aqueous sodium carbonate solution for 2 hours. The pH of the mixture was about 10. The heating was discontinued and the mixture was filtered, the filter cake was first washed with 5% aqueous sodium carbonate solution, and then with water. The solid product (300 mg) isolated was identified by HPLC to be 2-(2,4-dihydroxyphenyl)-4,6-bis(2,4-dimethylphenyl)-1,3,5-triazine, which was free of polyresorcinol-triazine impurities.

c. Isolation of Polyresorcinol-triazines

The filtrate from the part (b) above was cooled in an ice-bath and was acidified with aqueous hydrochloric acid. It was extracted with ethyl acetate. The organic layer was separated and was analyzed by HPLC to contain only polyresorcinol-triazines and no 2-(2,4-dihydroxyphenyl)-4,6-bis(2,4-dimethylphenyl)-1,3,5-triazine.

Example 8

Process to Isolate 2-(2,4-dihydroxyphenyl)-4,6-bis(2,4-dimethylphenyl)-1,3,5-triazine by Removing Both Polyresorcinol-triazines and Trisxylyl-triazine: Procedure 1

A: Removal of Polyresorcinol-triazines

To 10 gm crude 2-(2,4-dihydroxyphenyl)-4,6-bis(2,4-dimethylphenyl)-1,3,5-triazine (50% water wet) prepared by the procedure of WO 00/29392 containing polyresorcinol-triazines and trisxylyl-triazine as impurities was added 50 mL of 5% aqueous sodium carbonate in a flask equipped with magnetic stirrer, a nitrogen inlet and a reflux condenser. The mixture was heated to reflux for 2 hours. The pH of the mixture was about 10. The heating was discontinued, and the mixture was filtered, the filter cake washed with water, and dried to give 2-(2,4-dihydroxyphenyl)-4,6-bis(2,4-dimethylphenyl)-1,3,5-triazine which was analyzed by HPLC to be free of polyresorcinol-triazines, but had 11% trisxylyl-triazine impurity.

B: Removal of Trisxylyl-triazine 9.5 gm of the water wet 2-(2,4-dihydroxyphenyl)-4,6-bis(2,4-dimethylphenyl)-1,3,5-triazine obtained in Example 8a above was heated to reflux with 60 mL of heptane for 1 hour. The mixture was cooled, filtered and the filter cake washed with additional heptane. The HPLC of the 4 gm dry-solid product thus obtained showed it to be 2-(2,4-dihydroxyphenyl)-4,6-bis(2,4-dimethylphenyl)-1,3,5-triazine that was free of polyresorcinol-triazine impurities, and the trisxylyl-triazine was reduced to 0.3%.

Example 9

Process to Isolate 2-(2,4-dihydroxyphenyl)-4,6-bis(2,4-dimethylphenyl)-1,3,5-triazine by Removing Both Trisresorcinol-triazine and Trisxylyl-triazine: Procedure 2

A: Removal of Trisxylyl-triazine

A mixture of 10 gm of crude 2-(2,4-dihydroxyphenyl)-4,6-bis(2,4-dimethylphenyl)-1,3,5-triazine (50% wet) prepared by the procedure of WO 00/29392 containing 10% of trisxylyl-triazine and 4% polyresorcinol-triazines as impurities, and 70 mL heptane was heated to reflux for 1 hour. The mixture was cooled, filtered and the filter cake washed with additional heptane and dried to give 4.5 gm of 2-(2,4-dihydroxyphenyl)-4,6-bis(2,4-dimethylphenyl)-1,3,5-triazine which by HPLC analysis has only 0.9% trisxylyl-triazine remaining, but there was no change in the level of polyresorcinol-triazine impurity.

B: Removal of Polyresorcinol-triazines

To 4.5 gm of dry 2-(2,4-dihydroxyphenyl)-4,6-bis(2,4-dimethylphenyl)-1,3,5-triazine (containing polyresorcinol-triazines as impurities) obtained in Example 9A was added 25 mL of 5% aqueous sodium carbonate in a flask equipped with magnetic stirrer, a nitrogen inlet and a reflux condenser. The mixture was heated to reflux for 1 hour. The pH of the mixture was about 10. The heating was discontinued, and the mixture was filtered, the filter cake washed with water, and dried to give 4 gm of 2-(2,4-dihydroxyphenyl)-4,6-bis(2,4-dimethylphenyl)-1,3,5-triazine which was analyzed by HPLC to be free of polyresorcinol-triazines.

Example 10

Process to Isolate 2-(2,4-dihydroxyphenyl)-4,6-bis(2,4-dimethylphenyl)-1,3,5-triazine by Removing Trisxylyl-triazine A mixture of 20 gm of crude 2-(2,4-dihydroxyphenyl)-4,6-bis(2,4-dimethylphenyl)-1,3,5-triazine prepared by the procedure of WO 00/29392 (about 40% wet; which had been treated with 3% aqueous sodium carbonate to remove polyresorcinol-triazines), 20 mL toluene and 80 mL heptane was heated to reflux for 1 hour. The heating was discontinued and the mixture cooled to 30° C. The mixture was filtered, the filter cake washed with a mixture of 20 mL toluene and 80 mL heptane and dried to give 11.7 gm of 2-(2,4-dihydroxyphenyl)-4,6-bis(2,4-dimethylphenyl)-1,3,5-triazine which was analyzed by HPLC to be free of trisxylyl-triazine impurity.

Example 11

Removal of p-Chlorophenol Impurity from 2-(2,4-dihydroxyphenyl)-4,6-bis(2,4-dimethylphenyl)-1,3,5-triazine To a mixture of 5 gm of 2-(2,4-dihydroxyphenyl)-4,6-bis(2,4-dimethylphenyl)-1,3,5-triazine and 1 gm of p-chlorophenol was added 50 mL of 5% aqueous sodium carbonate solution. The mixture was heated to reflux for 3 hours. The heating was discontinued and the mixture was filtered, the filter cake washed first with 5% aqueous sodium carbonate solution and then with water. The HPLC of the solid product (4.9 gm) showed it to be 2-(2,4-dihydroxyphenyl)-4,6-bis(2,4-dimethylphenyl)-1,3,5-triazine with no detectable amount of p-chlorophenol remaining.

Example 12

Preparation of 2-(2,4-dihydroxyphenyl)-4,6-bis(3,4-dimethylphenyl)-1,3,5-triazine To a flask equipped with a reflux condenser, a nitrogen inlet, and a mechanical stirrer is added 50 gm of cyanuric chloride, 191 mL of ODCB and 108.4 gm of aluminum chloride. The mixture is cooled in an ice-bath to 5° C. and 6.5 gm of concentrated HCl was added over a period of 20 minutes. The mixture was allowed to warm to room temperature, and stirred for 2 hours. It was cooled back to 5° C. and then 54.7 gm of o-xylene was slowly added over a period of 3 hours, while allowing the temperature to go up to 21° C. The mixture was stirred at room temperature for additional 16 hours. The reaction mixture was heated to about 63° C. and 34 gm of resorcinol was added over a period of about 30 minutes. The mixture was held at about 75° C. for 3 hours. It was then added to 500 mL water and ODCB distilled off azeotropically. The precipitated solid was filtered off and washed with water. The material was dried in a vacuum oven to give 96 gm of crude 2-(2,4-dihydroxyphenyl)-4,6-bis(3,4-dimethylphenyl)-1,3,5-triazine. The HPLC analysis showed it to contain about 5% of polyresorcinol-triazines and 10.7% tris-o-xylyl-triazine.

Example 13

Isolation of 2-(2,4-dihydroxyphenyl)-4,6-bis(3,4-dimethylphenyl)-1,3,5-triazine: Procedure 1

A: Removal of Polyresorcinol-triazines

In a flask equipped with magnetic stirrer, a nitrogen inlet and a reflux condenser was added 5 gm crude 2-(2,4- dihydroxyphenyl)-4,6-bis(3,4-dimethylphenyl)-1,3,5-triazine containing polyresorcinol-triazines as impurities and 30 mL of 3% aqueous sodium carbonate. The mixture was heated to reflux for 2 hours. The pH of the mixture was about 10. The heating was discontinued, and the mixture was filtered, the filter cake washed with water to give 2-(2,4-dihydroxyphenyl)-4,6-bis(3,4-dimethylphenyl)-1,3,5-triazine which was analyzed by HPLC to be free of polyresorcinol-triazines, but had 11% trisxylyl-triazine impurity.

B: Removal of Tris-o-xylyl-triazine

In a flask equipped with a Dean-Stark apparatus, a nitrogen inlet and a magnetic stirring bar was added 11.4 gm of the wet filter cake in Example 13A containing 2-(2,4-dihydroxyphenyl)-4,6-bis(3,4-dimethylphenyl)-1,3,5-triazine was heated to reflux with 40 mL of toluene. Water was removed azeotropically. The heating was discontinued after 2 hours. The mixture was cooled, filtered and the filter cake washed with additional toluene to give 3.9 gm of the product. The HPLC of the solid product thus obtained showed it to be 2-(2,4-dihydroxyphenyl)-4,6-bis(3,4-dimethylphenyl)-1,3,5-triazine that was free of polyresorcinol impurities, and the tris-o-xylyl-triazine was reduced to 0.3%.

Example 14

Isolation of 2-(2,4-dihydroxyphenyl)-4,6-bis(3,4-dimethylphenyl)-1,3,5-triazine: Procedure 2

A: Removal of Tris-o-xylyl-triazine

A mixture of 5 gm of the crude 2-(2,4-dihydroxyphenyl)-4,6-bis(3,4-dimethylphenyl)-1,3,5-triazine prepared from the procedure in Example 13A was heated to reflux with 30 mL of toluene in a flask equipped with a nitrogen inlet and a magnetic stirring bar. The heating was discontinued after 2 hours. The mixture was cooled, filtered and the filter cake washed with additional toluene to give 4.1 gm of the product. The HPLC of the solid product thus obtained showed it to be 2-(2,4-dihydroxyphenyl)-4,6-bis(3,4-dimethylphenyl)-1,3,5-triazine that contained 3.9% polyresorcinol impurities, and the tris-o-xylyl-triazine was reduced to 1.6%.

B: Removal of Polyresorcinol-triazines

In a flask equipped with magnetic stirrer, a nitrogen inlet and a reflux condenser was added 4.1 gm of the above 2-(2,4-dihydroxyphenyl)-4,6-bis(3,4-dimethylphenyl)-1,3,5-triazine containing polyresorcinol-triazines as impurities and 30 mL of 3% aqueous sodium carbonate. The mixture was heated to reflux for 2 hours. The pH of the mixture was about 10. The heating was discontinued, and the mixture was filtered, the filter cake washed with 3% aqueous sodium carbonate followed by water to give 3.8 gm of 2-(2,4-dihydroxyphenyl)-4,6-bis(3,4-dimethylphenyl)-1,3,5-triazine which was analyzed by HPLC to be free of polyresorcinol-triazines, and had 1.7% tris-o-xylyl-triazine impurity.

Example 15

Isolation of 2-(2,4-dihydroxyphenyl)-4,6-bis(2,4-dimethylphenyl)-1,3,5-triazine by Treatment of its Solution with Aqueous Potassium Carbonate To a flask equipped with a reflux condenser, a nitrogen inlet, and a magnetic stirrer was added 50 mL of ethyl acetate and 5 gm of crude 2-(2,4-dihydroxyphenyl)-4,6-bis(2,4-dimethylphenyl)-1,3,5-triazine containing polyresorcinol-triazines as impurities and stirred at room temperature to form a solution. To it was then added 25 mL 5% aqueous potassium carbonate solution, and the contents stirred for 10 minutes at room temperature. The organic layer was then separated, washed with water twice and dried over anhydrous sodium sulfate. The solvent was then removed under reduced pressure to give 4.7 gm of 2-(2,4-dihydroxyphenyl)-4,6-bis(2,4-dimethylphenyl)-1,3,5-triazine which was analyzed by HPLC to contain no polyresorcinol-triazine impurities.

Example 16

Isolation of 2-(2,4-dihydroxyphenyl)-4,6-bis(2,4-dimethylphenyl)-1,3,5-triazine by Treatment of its Solution with Aqueous Triethylamine To a flask, 5 gm of 2-(2,4-dihydroxyphenyl)-4,6-bis(2,4-dimethylphenyl)-1,3,5-triazine containing polyresorcinol-triazine impurities was dissolved in 50 mL of ethyl acetate. To it was added 15 mL of 5% aqueous triethylamine solution. The mixture was stirred at room temperature for 10 minutes. The organic layer was separated, washed twice with water, dried over anhydrous $Na_2SO_4$ and solvent removed under reduced pressure to give 4.6 gm of 2-(2,4-dihydroxyphenyl)-4,6-bis(2,4-dimethylphenyl)-1,3,5-triazine, which was analyzed by HPLC to be free of polyresorcinol-triazine impurities.

Example 17

Isolation of 2-(2,4-dihydroxyphenyl)-4,6-bis(2,4-dimethylphenyl)-1,3,5-triazine by Treating it in Solid Form with Aqueous Triethylamine To a flask was added 5 gm of 2-(2,4-dihydroxyphenyl)-4,6-bis(2,4-dimethylphenyl)-1,3,5-triazine containing polyresorcinol-triazines as impurities and 25 mL of 5% aqueous triethylamine solution. The mixture was heated to 80° C. for 1 hour. The pH of the mixture was about 10. The heating was discontinued, and the mixture cooled to room temperature. It was then filtered, the filter cake washed first with 5% aqueous triethylamine solution and then with water, and dried to give 4.7 gm of 2-(2,4-dihydroxyphenyl)-4,6-bis(2,4-dimethylphenyl)-1,3,5-triazine, which was analyzed by HPLC to be free of polyresorcinol-triazine impurities.

Example 18

Isolation of 2-(2,4-dihydroxyphenyl)-4,6-bis(3,4-dimethylphenyl)-1,3,5-triazine by Treatment of the Solid Mixture with Aqueous Triethylamine A mixture of 5 gm of 2-(2,4-dihydroxyphenyl)-4,6-bis(3,4-dimethylphenyl)-1,3,5-triazine containing polyresorcinol-triazines as impurities and 25 mL of 5% aqueous triethylamine solution. The mixture was heated to 80° C. for 1 hour. It was cooled to room temperature, filtered, the filter cake washed first with 15 mL 5% aqueous triethylamine solution, followed by three 15 mL water washes. The filtered product (4.7 gm) was analyzed by HPLC to contain 2-(2,4-dihydroxyphenyl)-4,6-bis(3,4-dimethylphenyl)-1,3,5-triazine with no polyresorcinol-triazine detected.

Example 19

Isolation of 2-(2,4-dihydroxyphenyl)-4,6-bis(2,4-dimethylphenyl)-1,3,5-triazine by Treatment of the Solid Mixture with Aqueous Methanolic Triethylamine To a flask was added 5 gm of 2-(2,4-dihydroxyphenyl)-4,6-bis(2,4-dimethylphenyl)-1,3,5-triazine containing polyresorcinol-triazines as impurities and 25 mL of 5% triethylamine solution prepared in aqueous methanol (1:1). The mixture was heated to 60° C. for 1 hour. It was cooled to room temperature, filtered, the filter cake washed first with 15 mL 5% aqueous methanolic triethylamine solution, followed by three 15 mL water washes. The filtered product (4.6 gm) was analyzed by HPLC to contain 2-(2,4-dihydroxyphenyl)-4,6-bis(2,4-dimethylphenyl)-1,3,5-triazine with no polyresorcinol-triazine detected.

Example 20

Isolation of 2-(2,4-dihydroxyphenyl)-4,6-bis(2,4-dimethylphenyl)-1,3,5-triazine by Treatment of the Solid Mixture with Methanolic Triethylamine To a flask was added 5 gm of 2-(2,4-dihydroxyphenyl)-4,6-bis(2,4-dimethylphenyl)-1,3,5-triazine containing polyresorcinol-triazines as impurities and 25 mL of 5% triethylamine in methanol. The mixture was heated to 60° C. for 1 hour. It was cooled to room temperature, filtered, the filter cake washed first with 15 mL 5% methanolic triethylamine solution, followed by two 15 mL methanol washes. The filtered product (4.2 gm) was analyzed by HPLC to contain 2-(2,4-dihydroxyphenyl)-4,6-bis(2,4-dimethylphenyl)-1,3,5-triazine with no polyresorcinol-triazine detected.

Example 21

Isolation of 2-(2,4-dihydroxyphenyl)-4,6-bis(ethylphenyl)-1,3,5-triazine by Treatment of its Solution with Aqueous Sodium Carbonate To a flask equipped with a reflux condenser, a nitrogen inlet, and a magnetic stirrer was added 50 mL of ethyl acetate and 5 gm of crude 2-(2,4-dihydroxyphenyl)-4,6-bis(ethylphenyl)-1,3,5-triazine prepared by the procedure in WO 00/29392 containing polyresorcinol-triazines as impurities and stirred at room temperature to form a solution. To it was then added 25 mL 5% aqueous sodium carbonate solution, and the contents stirred for 10 minutes at room temperature. The organic layer was then separated, washed with water twice and dried over anhydrous sodium sulfate. The solvent was then removed under reduced pressure to give 4.6 gm of 2-(2,4-dihydroxyphenyl)-4,6-bis(ethylphenyl)-1,3,5-triazine which was analyzed by HPLC to contain no polyresorcinol-triazine impurities.

Example 22

Isolation of 2-(2,4-dihydroxyphenyl)-4,6-bis(methylphenyl)-1,3,5-triazine by Treatment with Aqueous Sodium Carbonate To a flask equipped with a reflux condenser, a nitrogen inlet, and a mechanical stirrer was added 30 mL of 5% aqueous sodium carbonate, and 5 gm of crude 2-(2,4-dihydroxyphenyl)-4,6-bis(methylphenyl)-1,3,5-triazine containing polyresorcinol-triazines as impurities prepared by the procedure in WO 00/29392. The resulting mixture was heated to reflux, and it was held at reflux for 1 hour. The pH of the mixture was about 10. The heating was discontinued, and the mixture was allowed to cool to room temperature. It was then filtered, the filter cake washed with 15 mL 5% aqueous sodium carbonate solution followed by three 20 mL water washes. The filtered product (4.7 gm) thus obtained was analyzed by HPLC to be 2-(2,4-dihydroxyphenyl)-4,6-bis(methylphenyl)-1,3,5-triazine free of polyresorcinol-triazine impurities.

Example 23

Isolation of 2-(2,4-dihydroxyphenyl)-4,6-bisphenyl-1,3,5-triazine by Treatment with Aqueous Sodium Carbonate To a flask equipped with a reflux condenser, a nitrogen inlet, and a mechanical stirrer was added 10 mL of 5% aqueous sodium carbonate, and 2 gm of crude 2-(2,4-dihydroxyphenyl)-4,6-bisphenyl-1,3,5-triazine containing polyresorcinol-triazines as impurities prepared by the procedure in WO 00/29392. The resulting mixture was heated to reflux, and it was held at reflux for 1 hour. The heating was discontinued, and the mixture was allowed to cool to room temperature. It was then filtered, the filter cake washed with 5 mL 5% aqueous sodium carbonate solution followed by three 10 mL water washes. The filtered product (1.8 gm) thus obtained was analyzed by HPLC to be 2-(2,4-dihydroxyphenyl)-4,6-bisphenyl-1,3,5-triazine free of polyresorcinol-triazine impurities.

Example 24

Isolation of 2-(2,4-dihydroxyphenyl)-4,6-bis(chlorophenyl)-1,3,5-triazine by Treatment with Aqueous Sodium Carbonate To a flask equipped with a reflux condenser, a nitrogen inlet, and a mechanical stirrer was added 30 mL of 5% aqueous sodium carbonate, and 5 gm of crude 2-(2,4-dihydroxyphenyl)-4,6-bis(chlorophenyl)-1,3,5-triazine containing polyresorcinol-triazines as impurities prepared by the procedure in WO 0029392. The resulting mixture was heated to reflux, and it was held at reflux for 1 hour. The heating was discontinued, and the mixture was allowed to cool to room temperature. It was then filtered, washed the filter cake with 15 mL 5% aqueous sodium carbonate solution followed by three 20 mL water washes. The filtered product (4.6 gm) thus obtained was analyzed by HPLC to be 2-(2,4-dihydroxyphenyl)-4,6-bis(chlorophenyl)-1,3,5-triazine-free of polyresorcinol-triazine impurities.

Example 25

Isolation of 2-(2,4-dihydroxyphenyl)-4,6-bis(2,4-dimethylphenyl)-1,3,5-triazine by Treating with Methanol to Remove Polyresorcinol-triazines To a flask equipped with a reflux condenser, a nitrogen inlet, and a mechanical or magnetic stirrer was added 6 gm of crude 2-(2,4-dihydroxyphenyl)-4,6-bis(2,4-dimethylphenyl)-1,3,5-triazine prepared by procedure in WO 00/29392 containing polyresorcinol-triazines as impurities and 60 mL of methanol. The mixture was heated to reflux for 1 hour. The heating was discontinued and the mixture allowed to cool to room temperature. It was then filtered, and the filter cake washed with 25 mL methanol. The filtered material (5.3 gm) was identified by HPLC to be 2-(2,4-dihydroxyphenyl)-4,6-bis(2,4-dimethylphenyl)-1,3,5-triazine containing no polyresorcinol-triazines.

What is claimed is:

1. A process for isolating a compound of Formula 1

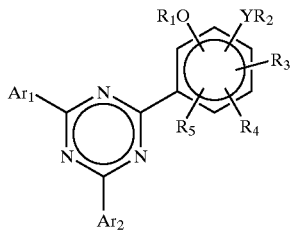

wherein Ar$_1$ and Ar$_2$ are the same or different and are radicals of the compound of Formula 2

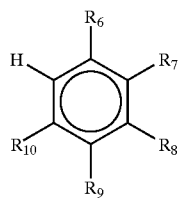

and wherein R$_1$ is hydrogen and R$_2$, R$_3$, R$_4$ and R$_5$, are the same or different and are hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, substituted or unsubstituted biphenylene, substituted or unsubstituted naphthalene, OR, NRR', CONRR', OCOR, CN, SR, SO$_2$R, and optionally with either of R$_3$ and R$_4$ or R$_4$ and R$_5$ taken together being a part of a saturated or unsaturated fused carbocyclic ring and wherein each R, R', R$_6$, R$_7$, R$_8$, R$_9$, and R$_{10}$ are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, substituted or unsubstituted biphenylene, substituted or unsubstituted naphthalene, and optionally with either of R$_6$ and R$_7$, R$_7$ and R$_8$, R$_8$ and R$_9$, or R$_9$ and R$_{10}$, taken together being a part of a saturated or unsaturated fused carbocyclic ring optionally having O, N, or S atoms in the ring, and R$_6$, R$_7$, R$_8$, R$_9$, and R$_{10}$, may be an alkoxy of 1 to 24 carbons, and Y is a direct bond, O, NR", or wherein R" is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms;

wherein said process comprises the step of:
contacting a product mixture with a base to form an isolation blend,
wherein said product mixture comprises said compound of Formula 1 and a polyphenolic-triazine compound.

2. The process of claim 1 wherein said base is an inorganic base.

3. The process of claim 2 wherein said inorganic base is selected from the group consisting of: LiOH, NaOH, KOH, Mg(OH)$_2$, Ca(OH)$_2$, Zn(OH)$_2$, Al(OH)$_3$, NH$_4$OH, Li$_2$CO$_3$, Na$_2$CO$_3$, K$_2$CO$_3$, MgCO$_3$, CaCO$_3$, ZnCO$_3$, (NH$_4$)$_2$CO$_3$, BaCO$_3$, CaMg(CO$_3$)$_2$, NaHCO3, KHCO3, (CaO), BaO, LiNH$_2$, NaNH$_2$, KNH$_2$, Mg(NH$_2$)$_2$, Ca(NH$_2$)$_2$, Zn(NH$_2$)$_2$, Al(NH$_2$)$_3$, NaH, CaH2, KH, LiH, and mixtures thereof.

4. The process of claim 1 wherein said base is an organic base.

5. The process of claim 4 wherein the organic base is an amine that is primary, secondary, tertiary, aliphatic, cyclic, acyclic, aromatic, heteroaromatic, or heterocyclic; or salts of primary amine, secondary amine, alcohol, or organic acid.

6. The process of claim 5 wherein said organic base is selected from the group consisting of the salts of CH$_3$O$^-$, CH$_3$CH$_2$O$^-$, CH$_3$CH$_2$CH$_2$O$^-$, (CH$_3$)$_2$CHO$^-$, ((CH$_3$)$_2$CH)$_2$CHO$^-$, CH$_3$CH$_2$CH$_2$CH$_2$O$^-$, (CH$_3$)$_3$CO$^-$, CH$_3$NH$^-$, CH$_3$CH$_2$NH$^-$, CH$_3$CH$_2$CH$_2$NH$^-$, (CH$_3$)$_2$CHNH$^-$, ((CH$_3$)$_2$CH)$_2$CHNH$^-$, CH$_3$CH$_2$CH$_2$CH$_2$NH$^-$, (CH$_3$)$_3$CNH$^-$, (CH$_3$)$_2$N$^-$, (CH$_3$CH$_2$)$_2$N$^-$, (CH$_3$CH$_2$CH$_2$)$_2$N$^-$, ((CH$_3$)$_2$CH)$_2$N$^-$, (((CH$_3$)$_2$CH)$_2$CH)$_2$N$^-$, (CH$_3$CH$_2$CH$_2$CH$_2$)$_2$N$^-$, ((CH$_3$)$_3$C)$_2$N$^-$, formate, acetate, propylate, butanoate, benzoate; and CH$_3$NH$_2$, CH$_3$CH$_2$NH$_2$, CH$_3$CH$_2$CH$_2$NH$_2$, (CH$_3$)$_2$CHNH$_2$, ((CH$_3$)$_2$CH)$_2$CHNH$_2$, CH$_3$CH$_2$CH$_2$CH$_2$NH$_2$, (CH$_3$)$_3$CNH$_2$, (CH$_3$)$_2$NH, (CH$_3$CH$_2$)$_2$NH, (CH$_3$CH$_2$CH$_2$)$_2$NH, ((CH$_3$)$_2$CH)$_2$NH, ((CH$_3$)$_2$CH)$_2$EtN, (((CH$_3$)$_2$CH)$_2$CH)$_2$NH, (CH$_3$CH$_2$CH$_2$CH$_2$)$_2$NH, ((CH$_3$)$_3$C)$_2$NH, (CH$_3$)$_3$N, (CH$_3$CH$_2$)$_3$N, (CH$_3$CH$_2$CH$_2$)$_3$N, ((CH$_3$)$_2$CH)$_3$N, (((CH$_3$)$_2$CH)$_2$CH)$_3$N, (CH$_3$CH$_2$CH$_2$CH$_2$)$_3$N, ((CH$_3$)$_3$C)$_3$N, pyrrolidine, piperidine, N-alkylpiperidine, piperazine, N-alkylpiperazine, N,N-dialkylpiperazine, morpholine, N-alkylmorpholine, imidazole, pyrrole, pyridine, lutidine, 4-N,N-dimethylaminopyridine, aniline, N,N-dialkylaniline, tetramethylenediamine and mixtures thereof.

7. The process of claim 1 wherein said product mixture is in a solid form.

8. The process of claim 1 wherein said base is dissolved in at least one first solvent.

9. The process of claim 8 where said first solvent is selected from the group consisting of: water, an alcohol, acetonitrile, tetrahydrofuran, toluene, heptane and mixtures thereof.

10. The process of claim 7 further comprising the step of filtering said isolation blend.

11. The process of claim 8 wherein said contacting step is at a temperature of between about 10° C. to about the reflux temperature.

12. The process of claim 1 wherein said contacting step is at a pH between about 7 to about 14.

13. The process of claim 10 further comprising the step of contacting a filtrate from said filtering step with an acid to isolate a polyphenolic-triazine compound.

14. The process of claim 1 wherein said product mixture is dissolved in at least one second solvent.

15. The process of claim 14 wherein said second solvent is selected from the group consisting of: methylisobutylketone, methylethylketone, cyclohexanone, ethyl acetate, butyl acetate, methylene chloride, chloroform, carbontetrachloride, 1,2-dichloroethane, chlorobenzene, dichlorobenzene, toluene, xylenes and mixtures thereof.

16. The process of claim 1 wherein said base is dissolved in at least one first solvent and said product mixture is dissolved in at least one second solvent, wherein said second solvent is substantially immiscible in said first solvent, and wherein at least two distinct layers are formed.

17. The process of claim 16 wherein at least one of said layers is aqueous-based and at least one of said layers is organic-based, wherein said process further comprises the step of separating said aqueous-based layer from said organic-based layer.

18. The process of claim 1 wherein said compound of Formula 1 is

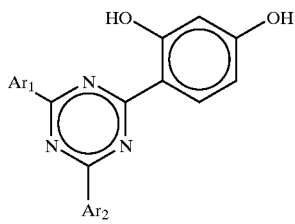

19. The process of claim 17 further comprising the steps of isolating a polyphenolic-triazine compound from said aqueous-based layer by contacting said aqueous-based layer with an acid;
and extracting said polyphenolic-triazine compound by solvent extraction.

20. A process for isolating a compound of Formula 1

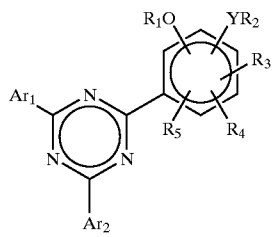

wherein $Ar_1$ and $Ar_2$ are the same or different and are radicals of the compound of Formula 2

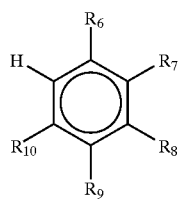

and wherein $R_1$ is hydrogen and $R_2$, $R_3$, $R_4$ and $R_5$, are the same or different and are hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, substituted or unsubstituted biphenylene, substituted or unsubstituted naphthalene, OR, NRR', CONRR', OCOR, CN, SR, $SO_2R$, and optionally with either of $R_3$ and $R_4$ or $R_4$ and $R_5$ taken together being a part of a saturated or unsaturated fused carbocyclic ring and wherein each R, R', $R_6$, $R_7$, $R_8$, $R_9$, and $R_{10}$ are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, substituted or unsubstituted biphenylene, substituted or unsubstituted naphthalene, and optionally with either of $R_6$ and $R_7$, $R_7$ and $R_8$, $R_8$ and $R_9$, or $R_9$ and $R_{10}$, taken together being a part of a saturated or unsaturated fused carbocyclic ring optionally having O, N, or S atoms in the ring, and $R_6$, $R_7$, $R_8$, $R_9$, and $R_{10}$, may be an alkoxy of 1 to 24 carbons, and Y is a direct bond, O, NR", or SRI!wherein R" is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms;

wherein said process comprises the steps of:
contacting a product mixture with an alcohol to form an isolation blend;
heating said isolation blend at a temperature of about 40° C. to about 200° C. for a period of 10 minutes to 10 hours,
wherein said product mixture comprises said compound of Formula 1 and a polyphenolic-triazine compound.

21. The process of claim 20 wherein said product mixture is in a solid form.

22. The process of claim 21 further comprising the step of filtering said isolation blend.

23. The process of claim 20 wherein said alcohol is selected from the group consisting of: methanol, ethanol, propanol, isopropanol, butanol, isobutanol, t-butanol, 1,2-ethanediol, 3-chloro-1-propanol, 2-hydroxyl-acetic acid, 1-hydroxyl-3-pentanone, cyclohexanol, cyclohexenol, glycerol, benzyl alcohol and mixtures thereof.

24. The process of claim 20 wherein the amount of said alcohol is about 1 to about 20 parts per part compound of Formula 1.

25. The process of claim 20 wherein said compound of Formula 1 is

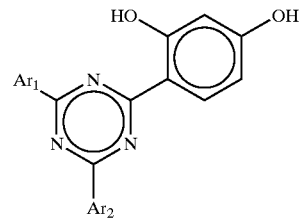

26. A process for isolating a compound of Formula 1

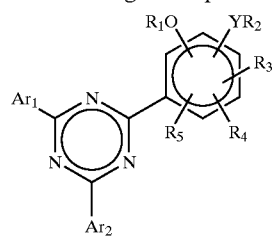

wherein $Ar_1$ and $Ar_2$ are the same or different and are radicals of the compound of Formula 2

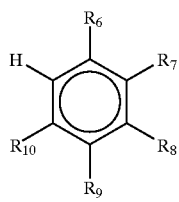

and wherein $R_1$ is hydrogen and $R_2$, $R_3$, $R_4$ and $R_5$, are the same or different and are hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, substituted or unsubstituted biphenylene, substituted or unsubstituted naphthalene, OR, NRR', CONRR', OCOR, CN, SR, $SO_2R$, and optionally with either of $R_3$ and $R_4$ or $R_4$ and $R_5$ taken together being a part of a saturated or unsaturated fused carbocyclic ring and wherein each R, R', $R_6$, $R_7$, $R_8$, $R_6$, and $R_{10}$ are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, substituted or unsubstituted biphenylene, substituted or unsubstituted naphthalene, and optionally with either of $R_6$ and $R_7$, $R_7$ and $R_8$, $R_8$ and $R_9$, or $R_9$ and $R_{10}$, taken together being a part of a saturated or unsaturated fused carbocyclic ring optionally having O, N, or S atoms in the ring, and $R_6$, $R_7$, $R_8$, $R_9$, and $R_{10}$, may be an alkoxy of 1 to 24 carbons, and Y is a direct bond, O, NR", or wherein R" is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms;

wherein said process comprises the step of:
contacting a product mixture with a hydrocarbon solvent to form an isolation blend, wherein said product mixture is in solid form and comprises said compound of Formula 1 and a trisaryl-triazine compound.

27. The process of claim 26 wherein said hydrocarbon solvent is selected from the group consisting of benzene, toluene, ethylbenzene, diethylbenzene, xylene, mesitylene, tetralin, hexane, heptane, octane, cyclohexane, and mixtures thereof.

28. The process of claim 26 wherein said contacting step is at a temperature of between about 10° C. to about the reflux temperature of said isolation blend.

29. The process of claim 26 further comprising filtering said isolation blend.

30. The process of claim 26 wherein the amount of said hydrocarbon solvent is about 1 to about 20 parts per part compound of Formula 1.

31. The process of claim 26 wherein said compound of Formula 1 is

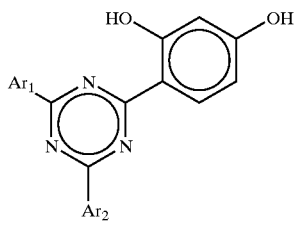

32. A process for isolating a compound of Formula 1

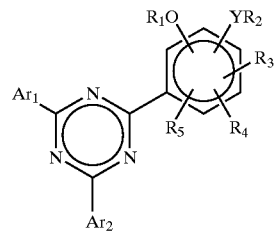

wherein $Ar_1$ and $Ar_2$ are the same or different and are radicals of the compound of Formula 2

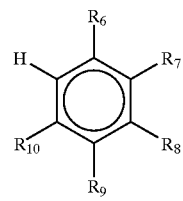

and wherein $R_1$ is hydrogen and $R_2$, $R_3$, $R_4$ and $R_5$, are the same or different and are hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, substituted or unsubstituted biphenylene, substituted or unsubstituted naphthalene, OR, NRR', CONRR', OCOR, CN, SR, $SO_2R$, and optionally with either of $R_3$ and $R_4$ or $R_4$ and $R_5$ taken together being a part of a saturated or unsaturated fused carbocyclic ring and wherein each R, R', $R_6$, $R_7$, $R_8$, $R_9$, and $R_{10}$ are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, substituted or unsubstituted biphenylene, substituted or unsubstituted naphthalene, and optionally with either of $R_6$ and $R_7$, $R_7$ and $R_8$, $R_8$ and $R_9$, or $R_9$ and $R_{10}$, taken together being a part of a saturated or unsaturated fused carbocyclic ring optionally having O, N, or S atoms in the ring, and $R_6$, $R_7$, $R_8$, $R_9$, and $R_{10}$, may be an alkoxy of 1 to 24 carbons, and Y is a direct bond, O, NR", or wherein R" is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms;

wherein said process comprises the step of:
contacting a product mixture with at least two components selected from the group consisting of a base, an alcohol and a hydrocarbon solvent,
wherein said product mixture comprises said compound of Formula 1 and a polyphenolic-triazine compound.

33. The process of claim 32 wherein said components are a base and a hydrocarbon solvent.

34. The process of claim 32 wherein said components are an alcohol and a hydrocarbon solvent.

35. The process of claim 32 wherein said contacting is performed in a step-wise manner.

36. The process of claim 32 wherein said contacting is performed in one-step manner.

37. The process of claim 32 wherein said compound of Formula 1 is

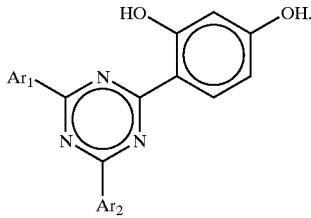

* * * * *

UNITED STATES PATENT AND TRADEMARK OFFICE
CERTIFICATE OF CORRECTION

PATENT NO. : 6,632,944 B2  Page 1 of 1
DATED : October 14, 2003
INVENTOR(S) : Gupta et al.

It is certified that error appears in the above-identified patent and that said Letters Patent is hereby corrected as shown below:

Column 23,
Line 51, after "or" insert -- S, --

Column 25,
Line 63, delete "SRI!" and insert -- S, --

Column 27,
Line 14, after "or" insert -- S, --

Column 28,
Line 35, after "or" insert -- S, --

Signed and Sealed this

Twenty-fifth Day of November, 2003

JAMES E. ROGAN
*Director of the United States Patent and Trademark Office*